US009603882B2

(12) United States Patent
Pan et al.

(10) Patent No.: US 9,603,882 B2
(45) Date of Patent: Mar. 28, 2017

(54) METHOD FOR MODULATING TH17 CELLS AND METHOD FOR TREATING A DISEASE RELATED TO MODULATION OF TH17 CELLS

(71) Applicant: Industrial Technology Research Institute, Hsinchu (TW)

(72) Inventors: I-Horng Pan, Hsinchu (TW);
Shu-Fang Wen, Hsinchu (TW);
Ming-Han Li, Taichung (TW);
Hsin-Jan Yao, Yunlin County (TW);
Hsin-Chieh Wu, Hsinchu (TW);
I-Huang Lu, Taipei (TW);
Joung-Liang Lan, Taipei (TW);
Der-Yuan Chen, Taichung (TW);
Chi-Chien Lin, Nantou (TW); Ching Lu, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 149 days.

(21) Appl. No.: 14/323,719

(22) Filed: Jul. 3, 2014

(65) Prior Publication Data
US 2015/0050315 A1 Feb. 19, 2015

(30) Foreign Application Priority Data

Aug. 13, 2013 (TW) .............................. 1021278941 A
Mar. 20, 2014 (CN) ........................... 2014 1 0104445

(51) Int. Cl.
*A61K 36/06* (2006.01)
*A61K 36/07* (2006.01)

(52) U.S. Cl.
CPC ................................... *A61K 36/07* (2013.01)

(58) Field of Classification Search
CPC ............................... A61K 36/06; A61K 36/07
USPC ........................................................ 424/195.15
See application file for complete search history.

(56) References Cited

U.S. PATENT DOCUMENTS

| 7,501,454 | B2 * | 3/2009 | Liu ...................... | C07C 403/02 514/690 |
| 7,932,285 | B2 | 4/2011 | Kuo et al. | |
| 8,110,191 | B2 | 2/2012 | Allan et al. | |
| 8,119,131 | B2 | 2/2012 | Di Padova et al. | |
| 8,148,420 | B2 | 4/2012 | Kuo et al. | |
| 9,017,697 | B2 * | 4/2015 | Thomas ................ | A61K 9/127 424/234.1 |
| 9,045,450 | B2 * | 6/2015 | Yang ..................... | C07D 307/88 |
| 2003/0180395 | A1 * | 9/2003 | Bueter ................... | A61K 36/67 424/725 |
| 2008/0312334 | A1 * | 12/2008 | Liu ...................... | C07C 403/02 514/690 |
| 2010/0227404 | A1 | 9/2010 | Wu et al. | |
| 2010/0279992 | A1 | 11/2010 | Lin | |
| 2011/0142831 | A1 | 6/2011 | Cua et al. | |
| 2012/0114678 | A1 | 5/2012 | Chen et al. | |

FOREIGN PATENT DOCUMENTS

| TW | 200848065 A | 12/2008 |
| TW | 201032816 A | 9/2010 |
| TW | 201036617 A | 10/2010 |

OTHER PUBLICATIONS

Alummo et al. Balance Between Regulatory T and Th17 Cells in Systemic Lupus Erythematosus: The Old and the New; Clinical and Developmental Immunology, vol. 2012, Article ID 823085, 5 pages.*
H.B. MacPhillamy: Drugs From Plants; Plant Science Bulletin, Botanical Society of America, vol. 9, No. 2, Apr. 1963.*
Phillipson, J. New Drugs From Nature—It Could Be Yew; Phytotherapy Research 13 (1999) pp. 2-8.*
Raskin et al. Can an Apple a Day Keep the Doctor Away? Current Pharmaceutical Design, 2004, 10, 3419-3429.*
Revilla et al. Comparison of Several Procedures Used for the Extraction of Anthocynains From Red Grapes; J. Agric. Food Chem. 1998, 46, pp. 4592-4597.*
Smet et al. Herbal Remedies; N Engl J Med, vol. 347, No. 25, Dec. 19, 2002, pp. 2046-2056.*
Ao et al. "Niuchangchih (*Antrodia camphorate* ) and its potential in treating liver diseases", J. Ethnopharmaco, 121, (2009), 194-212.
Bi et al. "Direct and Indirect Regulatory Mechanisms in TH17 cell Differentiation and Functions", Scan. J. Immunol. 75, 543-552.
Ghoreschi et al. "T helper 17 cell heterogeneity and pathogenicity in autoimmune disease", Trends Immunol. Sep. 2011; 32(9): 395-401.
Harrington et al. "Interleukin 17-producing CD4+ effector T cells develop via a lineage distinct from the T helper type 1 and 2 lineages", Nat. Immunol. 6, 1123-1132.
Langrish et al. "IL-23 drives a pathogenic T cell population that induces autoimmune inflammation", J. Exp. Med. (2005), vol. 201, No. 2, 233-240.
Liu et al. "A New Subset of CD4+T cells: Th17 and Its Biological Effects", Progress in Biochemistry and Biophysics, 2007, 34(4); 348-353.
Lu et al. "Active extracts of wild fruiting bodies of Antrodia camphorate (EEAC) induce leukemia Hl 60 cells apoptosis partially through histone hypoacetylation and synergistically promote anti-cancer effect of trichostatin A", Arch Toxicol (2009) 83:121-129.
Maddur et al. "Th17 Cells: Biology, Pathogenesis of Autoimmune and Inflammatory Diseases, and Therapeutic Strategies", The American Journal of Pathology, vol. 181, No. 1, Jul. 2012, 8-18.
Marwaha et al. "TH17 cells, in autoimmunity and immunodeficiency: protective or pathogenic?", Front. Immunol. 3, 129.
Office Action issued in Taiwan Patent Application No. 102128941 dated Apr. 21, 2014.
Park et al. "A distinct lineage of CD4 T cells regulates tissue inflammation by producing interleukin 17", Nat. Immunol. Nov. 2005; 6(11): 1133-1141.

(Continued)

*Primary Examiner* — Chris R Tate
(74) *Attorney, Agent, or Firm* — Birch, Stewart, Kolasch & Birch, LLP (57) ABSTRACT

The disclosure provides a method for modulating Th17 cells, including: administering an *Antrodia cinnamomea* (also named *Antrodia camphorata* or *Taiwanofungus camphoratus*) extract to a subject in need thereof, wherein the *Antrodia cinnamomea* extract has an effect of modulating Th17 cells. The *Antrodia cinnamomea* extract may include a fruiting body extract of *Antrodia cinnamomea* or a mycelium extract of *Antrodia cinnamomea*.

4 Claims, 6 Drawing Sheets

(56) References Cited

OTHER PUBLICATIONS

Sarah L. Gaffen "Recent advances in the IL-17 cytokine family", Curr. Opin. Immunol. Oct. 2011; 23(5): 613-619.
Wang et al. "Immunomodulatory and Anti-inflammatory Effects of Polysaccharides from Mycelia and Fermented Culture Broth of Antrodia camphorata", National Yang-Ming University Institute of Clinical Medicine Master Thesis, Jan. 2009, pp. 1-45.
Wilke et al. "Deciphering the role of Th17 cells in human disease", Trends Immunol. Dec. 2011; 32(12): 603-611.

* cited by examiner

METHOD FOR MODULATING TH17 CELLS AND METHOD FOR TREATING A DISEASE RELATED TO MODULATION OF TH17 CELLS

CROSS REFERENCE TO RELATED APPLICATION

The present application is based on, and claims priority from, Taiwan Application Serial Number 102128941, filed on Aug. 13, 2013, and from China Application Serial Number 201410104445.4, filed on Mar. 20, 2014, the disclosures of which are hereby incorporated by reference herein in its entirety.

TECHNICAL FIELD

The technical field relates to a method for modulating Th17 cells and a method for treating a disease related to modulation of Th17 cells.

BACKGROUND

Th17 cells belong to a unique group of $CD4^+$ T cells, and are considered as T cells which are able to produce IL-17A and IL-17F (Harrington et al., 2005; Park et al., 2005; Langrish et al., 2005). Differentiating from Th1 and Th2 cells, development of Th17 cells are regulated by TGF-β and other inflammatory cytokines, such as IL-6, IL-21, IL-1β and IL-23 (Bi and Yang, 2012). In addition to IL-17A and IL-17F, Th17 cells also can secrete other indicator cytokines, such as IL-21, IL-22, IFN-γ, IL-4, IL-10, IL-9, IL-26, CXCL8 and CCL20, etc. (Marwaha et al., 2012), and thus they can affect other cells, such as fibroblasts, keratinocytes, endothelial cells, neutrophils and memory T cells, etc. (Gaffen, 2011; Ghoreschi et al., 2011; Wilke et al., 2011). At present, it has been found that Th17 cells and the acting factors thereof, such as IL-17, IL-21, IL-22, GM-CSF and CCL20, etc. are related to pathogenesis of autoimmune diseases and inflammatory diseases, such as systemic lupus erythematosus (SLE), psoriasis, rheumatoid arthritis (RA), multiple sclerosis (MS), inflammatory bowel disease, allergy, asthma, etc. (Maddur et al., 2012).

*Antrodia cinnamomea* (also named *Antrodia camphorata* or *Taiwanofungus camphoratus*) is a traditional Chinese herb, which is a fungus endemic to Taiwan and only parasitizes in solid wood or on the moist surface of *Cinnamomum kanehirae* Hayata (Lauraceae) (Ao et al., 2009; Lu et al., 2009). At present, *Antrodia cinnamomea* has been applied to the treatment of hepatitis, cancers, abdominal pain, diarrhoea, hypertension, and used for liver protection, detoxification, etc. However, it is still not clear whether *Antrodia cinnamomea* has the effect of modulating Th17 cells or not.

SUMMARY

The disclosure provides a pharmaceutical composition for modulating Th17 cells, comprising: an *Antrodia cinnamomea* (also named *Antrodia camphorata* or *Taiwanofungus camphoratus*) extract as an active ingredient, wherein the *Antrodia cinnamomea* extract has an effect of modulating Th17 cells.

The disclosure also provides a method for modulating Th17 cells, comprising: administering an *Antrodia cinnamomea* extract to a subject in need thereof, wherein the *Antrodia cinnamomea* extract has an effect of modulating Th17 cells.

The disclosure also provides a method for treating a disease related to modulation of Th17 cells, comprising: administering an *Antrodia cinnamomea* extract to a subject in need thereof, wherein the *Antrodia cinnamomea* extract has an effect of inhibiting differentiation of Th17 cells.

A detailed description is given in the following embodiments with reference to the accompanying drawings.

BRIEF DESCRIPTION OF DRAWINGS

The present disclosure can be more fully understood by reading the subsequent detailed description and examples with references made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment of the present disclosure, a pharmaceutical composition for modulating Th17 cells may be provided. The pharmaceutical composition for modulating Th17 cells of the present disclosure may comprise an *Antrodia cinnamomea* extract as an active ingredient, but is not limited thereto.

In the pharmaceutical composition for modulating Th17 cells of the present disclosure, the *Antrodia cinnamomea* extract may have an effect of modulating Th17 cells. The effect of modulating Th17 cells mentioned above may comprise, for example, inhibiting or promoting differentiation, proliferation, etc. of Th17 cells, but is not limited thereto. In one embodiment, the effect of modulating Th17 cells mentioned above may comprise inhibiting differentiation of Th17 cells.

Moreover, in the pharmaceutical composition for modulating Th17 cells of the present disclosure, the *Antrodia cinnamomea* extract mentioned above may comprise a fruiting body extract of *Antrodia cinnamomea* or a mycelium extract of *Antrodia cinnamomea*.

The *Antrodia cinnamomea* extract mentioned above may be obtained by performing an extraction on a fruiting body or a mycelium of *Antrodia cinnamomea*, but it is not limited thereto. At least one extraction solvent may be used in the extraction process mentioned above.

In one embodiment, the preceding *Antrodia cinnamomea* extract is a fruiting body extract of *Antrodia cinnamomea*. In this embodiment, the fruiting body extract of *Antrodia cinnamomea* may be obtained by performing an extraction on a fruiting body of *Antrodia cinnamomea*, but is not limited thereto. At least one extraction solvent may be used in the extraction process mentioned above.

In this embodiment, the at least one extraction solvent mentioned above may comprise, but is not limited to, an alcohol and/or water, etc. Examples of the foregoing alcohol may comprise methanol, ethanol, isopropanol, butanol, etc., but is not limited thereto. In one embodiment, the foregoing alcohol is ethanol, and the ethanol mentioned above may comprise 10-95% ethanol aqueous solution, but it is not limited thereto. In addition, the ethanol mentioned above may be a 25%, 50% or 95% ethanol aqueous solution.

Furthermore, the preceding extraction process used to obtain the fruiting body extract of *Antrodia cinnamomea* may comprise the following steps, but it is not limited thereto.

First, a fruiting body of *Antrodia cinnamomea* is refluxed with the at least one extraction solvent mentioned above to form a mixture. In one embodiment, the time for refluxing may be about 0.5-8 hours. In one specific embodiment, the time for refluxing may be 1 hour.

Then, the mixture mentioned above is filtered to obtain a filtrate and a filtration residue, wherein the obtained filtrate may be a fruiting body extract of *Antrodia cinnamomea*.

In another embodiment, the preceding *Antrodia cinnamomea* extract is a mycelium extract of *Antrodia cinnamomea*. In this embodiment, the mycelium extract of *Antrodia cinnamomea* may be obtained by performing an extraction on a mycelium of *Antrodia cinnamomea*, but it is not limited thereto. At least one extraction solvent may be used in the extraction process mentioned above.

In this embodiment, the at least one extraction solvent mentioned above may comprise, but is not limited to ethyl acetate or acetone, etc. In one embodiment, the at least one extraction solvent is ethyl acetate while in another embodiment the at least one extraction solvent is acetone.

In addition, the preceding extraction process used to obtain the mycelium extract of *Antrodia cinnamomea* may comprise the following steps, but it is not limited thereto.

First, a mycelium of *Antrodia cinnamomea* is refluxed with the at least one extraction solvent mentioned above to form a mixture. In one embodiment, the time for refluxing may be about 0.5-8 hours. In one specific embodiment, the time for refluxing may be 1 hour.

After that, the mixture mentioned above is filtered to obtain a filtrate and a filtration residue, wherein the obtained filtrate may be a mycelium extract of *Antrodia cinnamomea*.

Furthermore, in one embodiment, the pharmaceutical composition for modulating Th17 cells of the present disclosure may further comprise a pharmaceutically acceptable carrier or salt.

In the pharmaceutical composition for modulating Th17 cells of the present disclosure, the pharmaceutically acceptable carrier mentioned above may comprise, but is not limited to, a solvent, a dispersion medium, a coating, an antibacterial and antifungal agent, or an isotonic and absorption delaying agent, etc. which is compatible to pharmaceutical administration. The pharmaceutical composition can be formulated into dosage forms for different administration routes utilizing conventional methods.

Moreover, the pharmaceutically acceptable salt mentioned above may comprise, but is not limited to, inorganic cation salt, such as alkali metal salts like sodium salt; potassium salt or amine salt, such as alkaline-earth metal salt like magnesium salt; or calcium salt, such as the salt containing bivalent or quadrivalent cation like zinc salt, aluminum salt or zirconium salt. In addition, the pharmaceutically acceptable salt may also comprise organic salt, such as dicyclohexylamine salt, methyl-D-glucamine, and amino acid salt such as arginine, lysine, histidine, or glutamine.

The pharmaceutical composition prepared according to the present disclosure may be administered orally, parenterally by an inhalation spray, or via an implanted reservoir. The parenteral method may comprise subcutaneous, intracutaneous, intravenous, intramuscular, intra-articular, intra-arterial, intrasynovial, intrasternal, intrathecal, and intralesional, as well as infusion techniques.

An oral composition can comprise, but is not limited to, tablets, capsules, emulsions, and aqueous suspensions, dispersions and solutions.

Moreover, in one embodiment, the pharmaceutical composition for modulating Th17 cells of the present disclosure may be used for treatment of a disease related to the modulation of Th17 cells, but is not limited thereto. Examples of the preceding disease related to the modulation of Th17 cells may comprise, but are not limited to, systemic lupus erythematosus (SLE), Graves' Disease, rheumatoid arthritis (RA), psoriasis, type 1 diabetes (T1DM), Hashimoto's thyroiditis, multiple sclerosis (MS), Parkinson's disease, inflammatory bowel disease, allergic diseases, acquired immunodeficiency disease, chronic obstructive pulmonary disease (COPD), atherosclerosis, myocarditis, dilated cardiomyopathy, cancers, etc.

In one embodiment, the pharmaceutical composition for modulating Th17 cells of the present disclosure may be used for treatment of systemic lupus erythematosus, Graves' Disease or psoriasis. The systemic lupus erythematosus mentioned above may comprise active systemic lupus erythematosus, but it is not limited thereto.

In another embodiment of the present disclosure, a method for modulating Th17 cells may be provided, wherein the *Antrodia cinnamomea* extract mentioned above may have an effect of modulating Th17 cells. The preceding effect of modulating Th17 cells mentioned above may comprise, but is not limited to, inhibiting or promoting Th17 cells differentiating, proliferating, etc. In one embodiment, the effect of modulating Th17 cells mentioned above may comprise inhibiting differentiation of Th17 cells.

In the method for modulating Th17 cells of the present disclosure, the *Antrodia cinnamomea* extract may comprise a fruiting body extract of *Antrodia cinnamomea* or a mycelium extract of *Antrodia cinnamomea*.

The *Antrodia cinnamomea* extract mentioned above may be obtained by performing an extraction on a fruiting body or a mycelium of *Antrodia cinnamomea*, but it is not limited thereto. At least one extraction solvent may be used in the preceding extraction process.

In one embodiment, the *Antrodia cinnamomea* extract mentioned above is a fruiting body extract of *Antrodia cinnamomea*. In this embodiment, the fruiting body extract of *Antrodia cinnamomea* may be obtained by performing an extraction on a fruiting body of *Antrodia cinnamomea*, but it is not limited thereto. At least one extraction solvent may be used in the extraction process mentioned above.

The at least one extraction solvent mentioned above may comprise an alcohol and/or water, etc., but it is not limited thereto. Suitable alcohol may comprise methanol, ethanol, isopropanol, butanol, etc., but it is not limited thereto. In one embodiment, the alcohol is ethanol, and the ethanol mentioned above may comprise 10-95% ethanol aqueous solution, but is not limited thereto. In addition, the ethanol mentioned above may be a 25%, 50% or 95% ethanol aqueous solution.

The preceding extraction process used to obtain the fruiting body extract of *Antrodia cinnamomea* may comprise the following steps, but it is not limited thereto.

First, a fruiting body of *Antrodia cinnamomea* is refluxed with the at least one extraction solvent mentioned above to form a mixture. In one embodiment, the time for refluxing may be about 0.5-8 hours. In one specific embodiment, the time for refluxing may be 1 hour.

Then, the mixture mentioned above is filtered to obtain a filtrate and a filtration residue, wherein the obtained filtrate may be a fruiting body extract of *Antrodia cinnamomea*.

In another embodiment, the *Antrodia cinnamomea* extract mentioned above is a mycelium extract of *Antrodia cinnamomea*. In this embodiment, the mycelium extract of *Antrodia cinnamomea* may be obtained by performing an extraction on a mycelium of *Antrodia cinnamomea*, but it is not limited thereto. At least one extraction solvent may be used in the extraction process mentioned above.

In this embodiment, the at least one extraction solvent mentioned above may comprise, but is not limited to, ethyl acetate or acetone, etc. In one embodiment, the at least one extraction solvent is ethyl acetate while in another embodiment, the at least one extraction solvent is acetone.

In addition, the preceding extraction process used to obtain the mycelium extract of *Antrodia cinnamomea* may comprise the following steps, but it is not limited thereto.

First, a mycelium of *Antrodia cinnamomea* is refluxed with the at least one extraction solvent mentioned above to form a mixture. In one embodiment, the time for refluxing may be about 0.5-8 hours. In one specific embodiment, the time for refluxing may be 1 hour.

After that, the mixture mentioned above is filtered to obtain a filtrate and a filtration residue, wherein the obtained filtrate may be a mycelium extract of *Antrodia cinnamomea*.

In another embodiment of the present disclosure, a method for treating a disease related to modulation of Th17 cells may be provided. The method for treating a disease related to modulation of Th17 cells may comprise administering an *Antrodia cinnamomea* extract to a subject in need thereof, wherein the *Antrodia cinnamomea* extract has an effect of inhibiting differentiation of Th17 cells. In one embodiment, the *Antrodia cinnamomea* extract is the *Antrodia cinnamomea* extract mentioned above.

Examples of the disease related to modulation of Th17 cells may comprise, but are not limited to, systemic lupus erythematosus (SLE), Graves' Disease, rheumatoid arthritis (RA), psoriasis, type 1 diabetes (T1DM), Hashimoto's thyroiditis, multiple sclerosis (MS), Parkinson's disease, inflammatory bowel disease, allergic diseases, acquired immunodeficiency disease, chronic obstructive pulmonary disease (COPD), atherosclerosis, myocarditis, dilated cardiomyopathy or cancers, etc.

In one embodiment, the disease related to modulation of Th17 cells mentioned above is systemic lupus erythematosus, Graves' Disease or psoriasis. Furthermore, the preceding systemic lupus erythematosus may comprise, for example, active systemic lupus erythematosus.

EXAMPLES

Example 1

Preparation of *Antrodia cinnamomea* Extract

1. Preparation of Fruiting Body Extract of *Antrodia cinnamomea*, ACFB03

The method for preparing ACFB03 sample is described in the following:

(1) 10 g powder of the fruiting body of *Antrodia cinnamomea* was added to 100 ml 95% ethanol aqueous solution to form a mixture, and then the mixture was refluxed for 1 hour.

(2) The mixture was centrifuged to remove the impurities therein (6000 rpm, 20 minutes) to collect the supernatant, and after that the supernatant was concentrated under reduced pressure to remove the solvent therein to obtain a dry extract.

(3) The dry extract was added to 20 ml pure water and sonicated to re-dissolve the dry extract and form a suspension.

(4) The suspension was lyophilized to remove the water.

(5) The lyophilized sample was collected for total of 1.67 g. The lyophilized sample was numbered as ACFB03.

2. Preparation of Fruiting Body Extract of *Antrodia cinnamomea*, ACFB06

The method for preparing ACFB06 sample is described in the following:

(1) 10 g powder of the fruiting body of *Antrodia cinnamomea* was added to 100 ml 25% ethanol aqueous solution to form a mixture, and then the mixture was refluxed for 1 hour.

(2) The mixture was centrifuged to remove the impurities therein (6000 rpm, 20 minutes) to collect the supernatant, and after that the supernatant was concentrated under reduced pressure to remove the solvent therein to obtain a dry extract.

(3) The dry extract was added to 20 ml pure water and sonicated to re-dissolve the dry extract and form a suspension.

(4) The suspension was lyophilized to remove the water.

(5) The lyophilized sample was collected for total of 0.59 g. The lyophilized sample was numbered as ACFB06.

3. Preparation of Fruiting Body Extract of *Antrodia cinnamomea*, ACFB12

The method for preparing ACFB06 sample is described in the following:

(1) 80 g powder of the fruiting body of *Antrodia cinnamomea* was added to 800 ml 50% ethanol aqueous solution to form a mixture, and then the mixture was refluxed for 1 hour.

(2) The mixture was filtered under reduced pressure with a filter paper (Toyo, NO. 2) while the mixture was still hot to collect the filtrate and obtain a residue of fruiting body of

*Antrodia cinnamomea* (filtration residue). The filtration under reduced pressure was maintained for 30 minutes to dry the residue of fruiting body of *Antrodia cinnamomea*.

(3) The residue of the fruiting body of *Antrodia cinnamomea* was recycled and added to 1600 ml pure water to form a mixture, and then the mixture was refluxed for 1 hour.

(4) The mixture was filtered under reduced pressure with a filter paper (Toyo, NO. 2) while the mixture was still hot to collect the filtrate.

(5) The two filtrates mentioned above were collected and concentrated under reduced pressure. The filtrate of step (2) was concentrated first. While the step of concentrating the filtrate of step (2) was being performed, the filtrate of step (4) was incorporated into the filtrate of step (2) and concentrated under reduced pressure to an appropriate concentration, and then lyophilized to remove the water.

(6) The lyophilized sample was collected for total of 20.34 g. The lyophilized sample was numbered as ACFB12.

4. Preparation of Mycelium Extract of *Antrodia cinnamomea*, AC06-EA (Ethyl Acetate Extract)

The method for preparing AC06-EA sample is described in the following:

(1) 2 g powder of mycelium of *Antrodia cinnamomea* was added to 30 ml ethyl acetate to form a mixture, and then the mixture was refluxed for 1 hour.

(2) The mixture was centrifuged to remove the impurities therein (6000 rpm, 10 minutes) and filtered with a filter paper (Toyo, NO. 2) to collect the filtrate, and after that the filtrate was concentrated under reduced pressure to remove the solvent therein to obtain an extract.

(3) The extract sample was collected for total of 0.32 g. The extract sample was numbered as AC06-EA.

5. Preparation of Mycelium Extract of *Antrodia cinnamomea*, AC06-A (Acetone extract)

The method for preparing AC06-A sample is described in the following:

(1) 2 g powder of mycelium of *Antrodia cinnamomea* was added to 30 ml acetone to form a mixture, and then the mixture was refluxed for 1 hour.

(2) The mixture was centrifuged to remove the impurities therein (6000 rpm, 10 minutes) and filtered with a filter paper (Toyo, NO. 2) to collect the filtrate, and after that the filtrate was concentrated under reduced pressure to remove the solvent therein to obtain an extract.

(3) The extract sample was collected for total of 0.30 g. The extract sample was numbered as AC06-A.

Example 2

Evaluation of Ability of Fruiting Body Extract of *Antrodia cinnamomea* to Inhibit Differentiation of Th17 Cells In this example, through a Th17 cell differentiation system established by mouse spleen cells, the effect of the fruiting body extract of *Antrodia cinnamomea* obtained from Example 1 (ACFB12, ACFB03 and ACFB06) on differentiation of Th17 cells was evaluated.

1. Evaluation of Ability of Fruiting Body Extract of *Antrodia cinnamomea*, ACFB03, to Inhibit Differentiation of Th17 Cells Spleen of a C57BL/6 mouse (6-8 weeks old) was taken out and ground with a mesh, and then a cell suspension was collected as primary spleen cells. Then, CD4$^+$ T cells were isolated by IMag magnetic system (BD Pharmingen, San Jose, Calif.), and the cells were added to a 24-well cell culture plate with a density of $5 \times 10^5$ cells/well. The preceding cells were grouped into five groups which were the naïve group, control group, experimental group A, experimental group B and experimental group C. Detailed treatments for the respective groups are shown in Table 1.

TABLE 1

Detailed treatments for respective groups

| Treatment reagent | Experimental group A | Experimental group B | Experimental group C | Control group | Naïve group |
|---|---|---|---|---|---|
| ACFB03 (µg/ml) | 20 | 10 | 5 | – | – |
| IL-6 (20 ng/ml) | + | + | + | + | – |
| TGF-β (20 ng/ml) | + | + | + | + | – |
| Anti-IFN-γ antibody (5 ng/ml) | + | + | + | + | – |
| Anti-IL-4 antibody (5 ng/ml) | + | + | + | + | – |
| Anti-IL-2 antibody (5 ng/ml) | + | + | + | + | – |

See Table 1. The naïve group was a group without any treatment reagent added thereto. The control group was a Th17 cell differentiation group, and cytokines and antibodies were applied thereto to promote the CD4$^+$ T cells differentiating into Th17 cells. For Experimental group A, Experimental group B and Experimental group C, the fruiting body extracts of *Antrodia cinnamomea* (ACFB03) at different concentrations were added to Experimental group A, Experimental group B and Experimental group C, respectively at the same time to observe the effects of the fruiting body extracts of *Antrodia cinnamomea* at different concentrations on the differentiation of Th17 cells. The cells mentioned above were cultured in an incubator containing 5% $CO_2$ at 37° C. After culturing for 3 days, 10 µl PMA (0.05 mg/ml) (Sigma) and 1 µl brefeldin A (eBioscience) were added to each well to stimulate the cells therein for 4 hours. After that the cells and the supernatants were collected, separately. The cells were fixed and permeabilized by Fixation & Permeabilization Buffers (eBioscience). After that, the cells were stained with anti-mouse IL-17 FITC antibody (0.25 µg/test) (eBioscience) and the Th17 cell percentage thereof was analyzed by a flow cytometer (Partec). The results are shown in FIG. 1.

Figure 1:
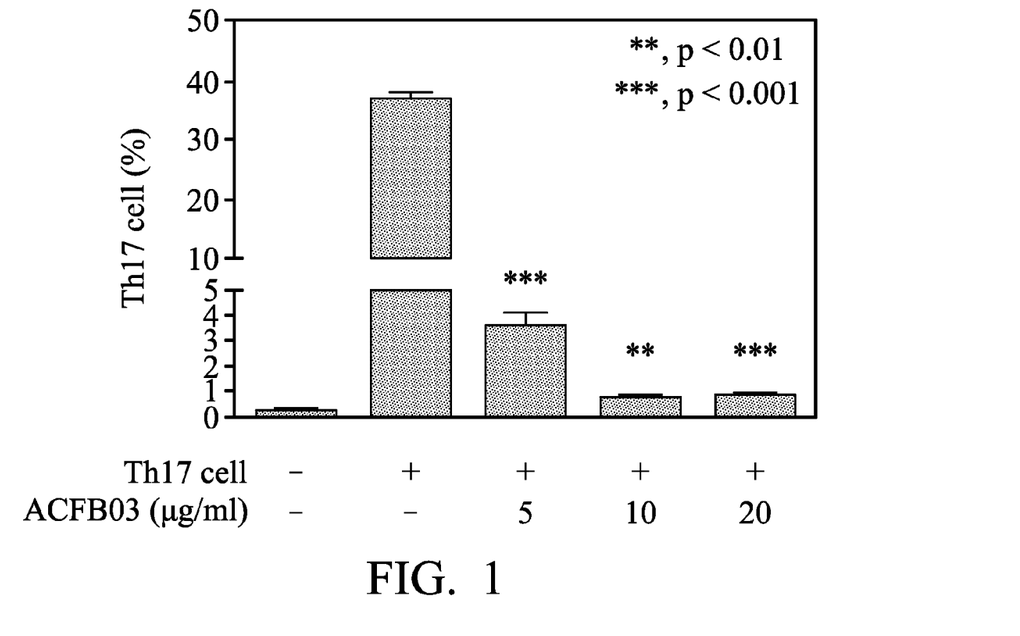
FIG. 1 shows the effect of *Antrodia cinnamomea* extract, ACFB03, on differentiation of Th17 cells according to one embodiment of the invention, : $p<0.01$, *: $p<0.001$.

FIG. 1 shows, in the experimental groups, the treatment of the fruiting body extracts of *Antrodia cinnamomea* (ACFB03) is capable of inhibiting differentiation of Th17, and under both treatments with concentrations of 10 µg/ml and 20 µg/ml, there are good inhibiting effects which can almost completely inhibit differentiation of Th17.

2. Evaluation of Ability of Fruiting Body Extract of *Antrodia cinnamomea*, ACFB06, to Inhibit Differentiation of Th17 Cells Spleen of a C57BL/6 mouse (6-8 weeks old) was taken out and ground with a mesh, and then a cell suspension was collected as primary spleen cells. Then, CD4$^+$ T cells were isolated by IMag magnetic system (BD Pharmingen, San Jose, Calif.), and the cells were added to a 24-well cell culture plate with a density of $5 \times 10^5$ cells/well. The preceding cells were grouped into five groups which were the naïve group, control group, experimental group D, experimental group E and experimental group F. Detailed treatments for the respective groups are shown in Table 2.

TABLE 2

Detailed treatments for respective groups

| Treatment reagent | Group | | | | |
|---|---|---|---|---|---|
| | Experimental group D | Experimental group E | Experimental group F | Control group | Naïve group |
| ACFB06 (μg/ml) | 20 | 10 | 5 | – | – |
| IL-6 (20 ng/ml) | + | + | + | + | – |
| TGF-β (20 ng/ml) | + | + | + | + | – |
| Anti-IFN-γ antibody (5 ng/ml) | + | + | + | + | – |
| Anti-IL-4 antibody (5 ng/ml) | + | + | + | + | – |
| Anti-IL-2 antibody (5 ng/ml) | + | + | + | + | – |

See Table 2. The naïve group was a group without any treatment reagent added thereto. The control group was a Th17 cell differentiation group, and cytokines and antibodies were applied thereto to promote the CD4$^+$ T cells differentiating into Th17 cells. For Experimental group D, Experimental group E and Experimental group F, fruiting body extracts of *Antrodia cinnamomea* (ACFB06) at different concentrations were added to Experimental group D, Experimental group E and Experimental group F, respectively at the same time to observe the effects of the fruiting body extracts of *Antrodia cinnamomea* at different concentrations on the differentiation of Th17 cells. The cells mentioned above were cultured in an incubator containing 5% $CO_2$ at 37° C. After culturing for 3 days, 10 μl PMA (0.05 mg/ml) (Sigma) and 1 μl brefeldin A (eBioscience) were added to each well to stimulate the cells therein for 4 hours. After that, the cells and the supernatants were collected, separately. The cells were fixed and permeabilized by Fixation & Permeabilization Buffers (eBioscience). After that, the cells were stained with anti-mouse IL-17 FITC antibody (0.25 μg/test)(eBioscience) and the Th17 cell percentage thereof was analyzed by a flow cytometer (Partec). The results are shown in FIG. 2.

Figure 2:
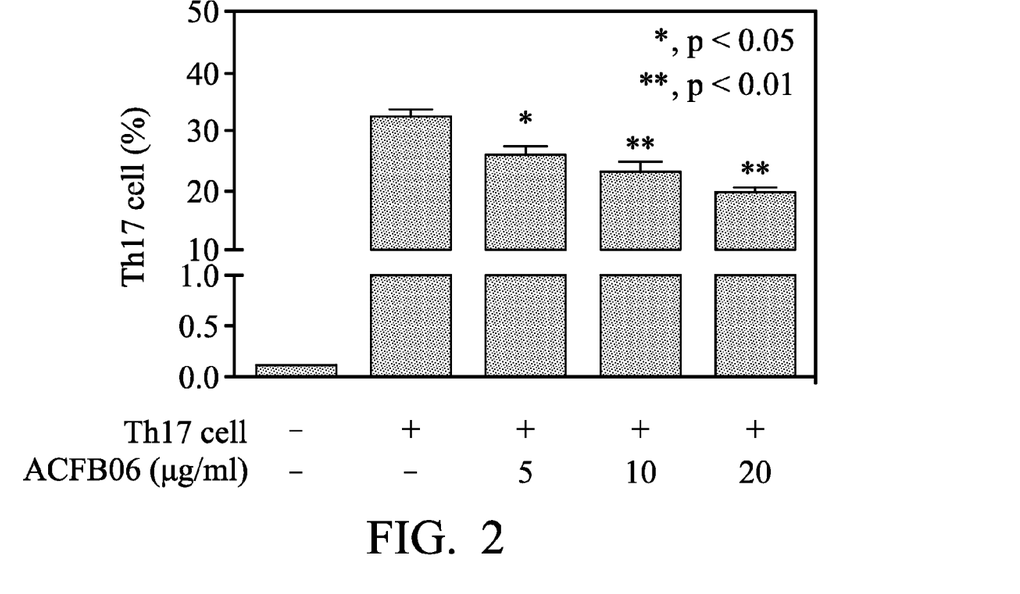
FIG. 2 shows the effect of *Antrodia cinnamomea* extract, ACFB06, on differentiation of Th17 cells according to one embodiment of the invention, *: $p<0.05$, **: $p<0.01$.

FIG. 2 shows, in the experimental groups, treatment of the fruiting body extracts of *Antrodia cinnamomea* (ACFB06) is also capable of inhibiting differentiation of Th17.

3. Evaluation of Ability of Fruiting Body Extract of *Antrodia cinnamomea*, ACFB12, to Inhibit Differentiation of Th17 Cells Spleen of a C57BL/6 mouse (6-8 weeks old) was taken out and ground with a mesh, and then a cell suspension was collected as primary spleen cells. Then, CD4$^+$ T cells were isolated by IMag magnetic system (BD Pharmingen, San Jose, Calif.), and the cells were added to a 24-well cell culture plate with a density of 5×10$^5$ cells/well. The preceding cells were grouped into five groups which were the naïve group, control group, experimental group G, experimental group H and experimental group I. Detailed treatments for the respective groups are shown in Table 3.

TABLE 3

Detailed treatments for respective groups

| Treatment reagent | Group | | | | |
|---|---|---|---|---|---|
| | Experimental group G | Experimental group H | Experimental group I | Control group | Naïve group |
| ACFB12 (μg/ml) | 20 | 10 | 5 | – | – |
| IL-6 (20 ng/ml) | + | + | + | + | – |
| TGF-β (20 ng/ml) | + | + | + | + | – |
| Anti-IFN-γ antibody (5 ng/ml) | + | + | + | + | – |
| Anti-IL-4 antibody (5 ng/ml) | + | + | + | + | – |
| Anti-IL-2 antibody (5 ng/ml) | + | + | + | + | – |

See Table 3. The naïve group was a group without any treatment reagent added thereto. The control group was a Th17 cell differentiation group, and cytokines and antibodies were applied thereto to promote the CD4$^+$ T cells differentiating into Th17 cells. For Experimental group G, Experimental group H and Experimental group I, fruiting body extracts of *Antrodia cinnamomea* (ACFB12) at different concentrations were added to Experimental group G, Experimental group H and Experimental group I, respectively at the same time to observe the effects of the fruiting body extracts of *Antrodia cinnamomea* at different concentrations on the differentiation of Th17 cells. The cells mentioned above were cultured in an incubator containing 5% $CO_2$ at 37° C. After culturing for 3 days, 10 μl PMA (0.05 mg/ml) (Sigma) and 1 μl brefeldin A (eBioscience) were added to each well to stimulate the cells therein for 4 hours. After that the cells and the supernatants were collected, separately. The cells were fixed and permeabilized by Fixation & Permeabilization Buffers (eBioscience). After that, the cells were stained with anti-mouse IL-17 FITC antibody (0.25 μg/test)(eBioscience) and the Th17 cell percentage thereof was analyzed by a flow cytometer (Partec). The results are shown in FIG. 3.

Figure 3:
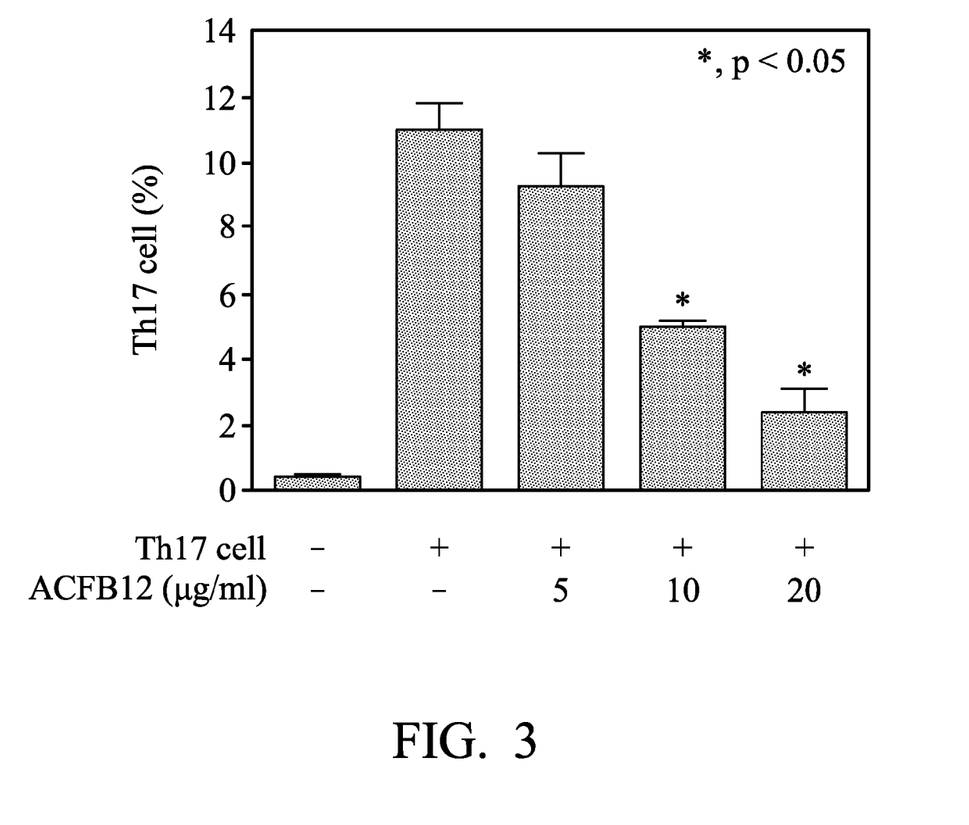
FIG. 3 shows the effect of *Antrodia cinnamomea* extract, ACFB12, on differentiation of Th17 cells according to one embodiment of the invention, *: $p<0.05$.

FIG. 3 shows, in the experimental groups, treatment of the fruiting body extracts of *Antrodia cinnamomea* (ACFB12) is also capable of inhibiting differentiation of Th17 cells. The inhibiting effect is increased in a dose-dependent manner. Especially under concentrations of 10 μg/ml and 20 μg/ml, the inhibiting effects are more significant.

According to the results shown in FIGS. 1-3, the inhibiting effect of the fruiting body extract of *Antrodia cinnamomea*, ACFB06, on differentiation of Th17 cells is weaker than those of the fruiting body extracts of *Antrodia cinnamomea*, ACFB12 and ACFB03.

Example 3

Evaluation of Ability of Mycelium Extract of *Antrodia cinnamomea* to Inhibit Differentiation of Th17 Cells In this example, through a Th17 cell differentiation system established by mouse spleen cells, effect of mycelium extract of *Antrodia cinnamomea* obtained from Example 1 (AC06-EA and AC06-A) on differentiation of Th17 cells was evaluated.

1. Evaluation of Ability of Mycelium Extract of *Antrodia cinnamomea*, AC06-EA, to Inhibit Differentiation of Th17 Cells Spleen of a C57BL/6 mouse (6-8 weeks old) was taken out and ground with a mesh, and then a cell suspension was collected as primary spleen cells. Then, CD4$^+$ T cells were isolated by IMag magnetic system (BD Pharmingen, San Jose, Calif.), and the cells were added to a 24-well cell culture plate with a density of 5×10$^5$ cells/well. The preceding cells were grouped into five groups which were the naive group, control group, experimental group J, experimental group K and experimental group L. Detailed treatments for the respective groups are shown in Table 4.

TABLE 4

Detailed treatments for respective groups

| Treatment reagent | Experimental group J | Experimental group K | Experimental group L | Control group | Naïve group |
|---|---|---|---|---|---|
| AC06-EA (μg/ml) | 20 | 10 | 5 | – | – |
| IL-6 (20 ng/ml) | + | + | + | + | – |
| TGF-β (20 ng/ml) | + | + | + | + | – |
| Anti-IFN-γ antibody (5 ng/ml) | + | + | + | + | – |
| Anti-IL-4 antibody (5 ng/ml) | + | + | + | + | – |
| Anti-IL-2 antibody (5 ng/ml) | + | + | + | + | – |

See Table 4. The naïve group was a group without any treatment reagent added thereto. The control group was a Th17 cell differentiation group, and cytokines and antibodies were applied thereto to promote the CD4$^+$ T cells differentiating into Th17 cells. For Experimental group J, Experimental group K and Experimental group L, the mycelium extracts of *Antrodia cinnamomea* (AC06-EA) at different concentrations were added to Experimental group J, Experimental group K and Experimental group L, respectively at the same time to observe the effects of the mycelium extracts of *Antrodia cinnamomea* at different concentrations on the differentiation of Th17 cells. The cells mentioned above were cultured in an incubator containing 5% CO$_2$ at 37° C. After culturing for 3 days, 10 μl PMA (0.05 mg/ml) (Sigma) and 1 μl brefeldin A (eBioscience) were added to each well to stimulate the cells therein for 4 hours. After that the cells and the supernatants were collected, separately. The cells were fixed and permeabilized by Fixation & Permeabilization Buffers (eBioscience). After that, the cells were stained with anti-mouse IL-17 FITC antibody (0.25 μg/test) (eBioscience) and the Th17 cell percentage thereof was analyzed by a flow cytometer (Partec). The results are shown in FIG. 4.

Figure 4:
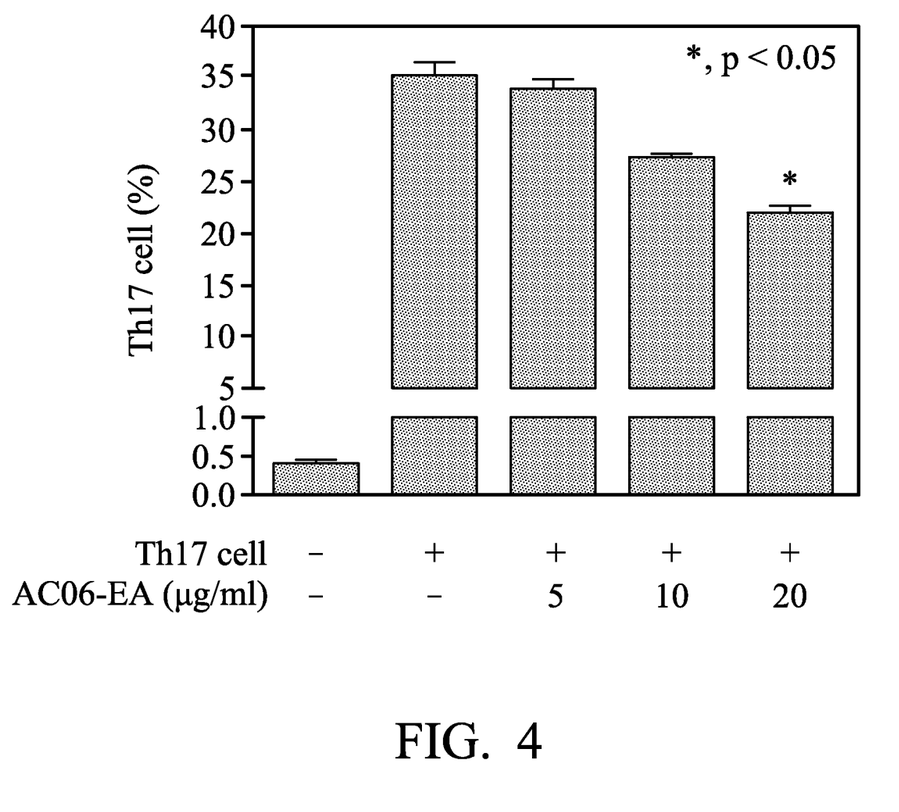
FIG. 4 shows the effect of *Antrodia cinnamomea* extract, AC06-EA, on differentiation of Th17 cells according to one embodiment of the invention, *: $p<0.05$.

FIG. 4 shows, in the experimental groups, treatment of mycelium extracts of *Antrodia cinnamomea* (AC06-EA) is capable of inhibiting the differentiation of Th17 cells. The inhibiting effect is increased in a dose-dependent manner. Especially under a concentration of 20 μg/ml, the inhibiting effect is more significant.

2. Evaluation of Ability of Mycelium Extract of *Antrodia cinnamomea*, AC06-A, to Inhibit Differentiation of Th17 Cells Spleen of a C57BL/6 mouse (6-8 weeks old) was taken out and ground with a mesh, and then a cell suspension was collected as primary spleen cells. Then, CD4$^+$ T cells were isolated by IMag magnetic system (BD Pharmingen, San Jose, Calif.), and the cells were added to a 24-well cell culture plate with a density of 5×10$^5$ cells/well. The preceding cells were grouped into five groups which were the naïve group, control group, experimental group M, experimental group N and experimental group O. Detailed treatments for the respective groups are shown in Table 5.

TABLE 5

Detailed treatments for respective groups

| Treatment reagent | Experimental group M | Experimental group N | Experimental group O | Control group | Naïve group |
|---|---|---|---|---|---|
| AC06-A (μg/ml) | 20 | 10 | 5 | – | – |
| IL-6 (20 ng/ml) | + | + | + | + | – |
| TGF-β (20 ng/ml) | + | + | + | + | – |
| Anti-IFN-γ antibody (5 ng/ml) | + | + | + | + | – |
| Anti-IL-4 antibody (5 ng/ml) | + | + | + | + | – |
| Anti-IL-2 antibody (5 ng/ml) | + | + | + | + | – |

See Table 5. The naïve group was a group without any treatment reagent added thereto. The control group was a Th17 cell differentiation group, and cytokines and antibodies were applied thereto to promote the CD4$^+$ T cells differentiating into Th17 cells. For Experimental group M, Experimental group N and Experimental group O, the mycelium extracts of *Antrodia cinnamomea* (AC06-A) at different concentrations were added to Experimental group M, Experimental group N and Experimental group O, respectively, at the same time to observe the effects of the mycelium extracts of *Antrodia cinnamomea* at different concentrations on the differentiation of Th17 cells. The cells mentioned above were cultured in an incubator containing 5% CO$_2$ at 37° C. After culturing for 3 days, 10 μl PMA (0.05 mg/ml) (Sigma) and 1 μl brefeldin A (eBioscience) were added to each well to stimulate the cells therein for 4 hours. After that the cells and the supernatant were collected, separately. The cells were fixed and permeabilized by Fixation & Permeabilization Buffers (eBioscience). After that, the cells were stained with anti-mouse IL-17 FITC antibody (0.25 μg/test) (eBioscience) and the Th17 cell percentage thereof was analyzed by a flow cytometer (Partec). The results are shown in FIG. 5.

Figure 5:
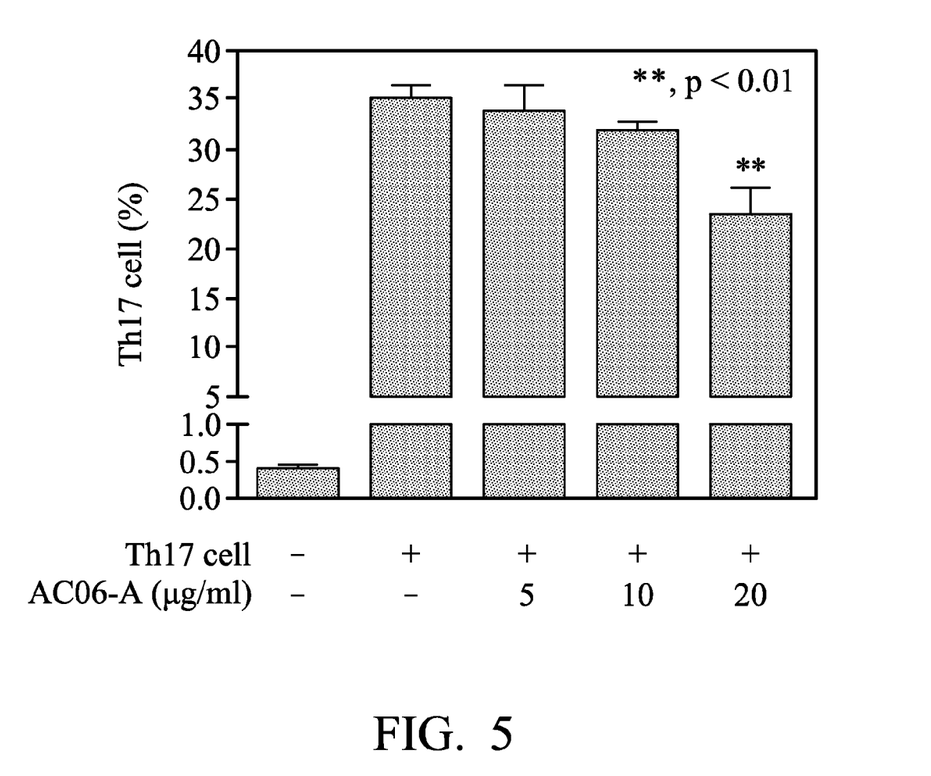
FIG. 5 shows the effect of *Antrodia cinnamomea* extract, AC06-A, on differentiation of Th17 cells according to one embodiment of the invention, **: $p<0.01$.

FIG. 5 shows, in the experimental groups, treatments of mycelium extract of *Antrodia cinnamomea*, AC06-A, are capable of inhibiting differentiation of Th17 cells, and the inhibiting effect thereof is similar to that of treatment of mycelium extracts of *Antrodia cinnamomea*, AC06-EA.

Example 4

Effect of Fruiting Body Extract of *Antrodia cinnamomea*, ACFB12, on Th17 Cells of Systemic Lupus Erythematosus (SLE) Patient In this experiment, through peripheral blood mononuclear cells (PBMCs) of a systemic lupus erythematosus patient, the effect of the fruiting body extract of *Antrodia cinnamomea*, ACFB12, on activity of Th17 cells of a systemic lupus erythematosus patient was evaluated. The procedure for the experiment is shown in the following:

Peripheral blood of 21 active systemic lupus erythematosus patients and 20 healthy people was treated with ACFB12 (20 ng/ml) (experimental group) or DMSO (control group) for 6 hours, and then the mononuclear cells therein were isolated. After that, intracellular staining was performed to the mononuclear cells with the IL-17 antibody. Finally the stained mononuclear cells were analyzed to determine the percentage of Th17 cells present therein. The experimental results are shown in FIG. 6.

Figure 6:
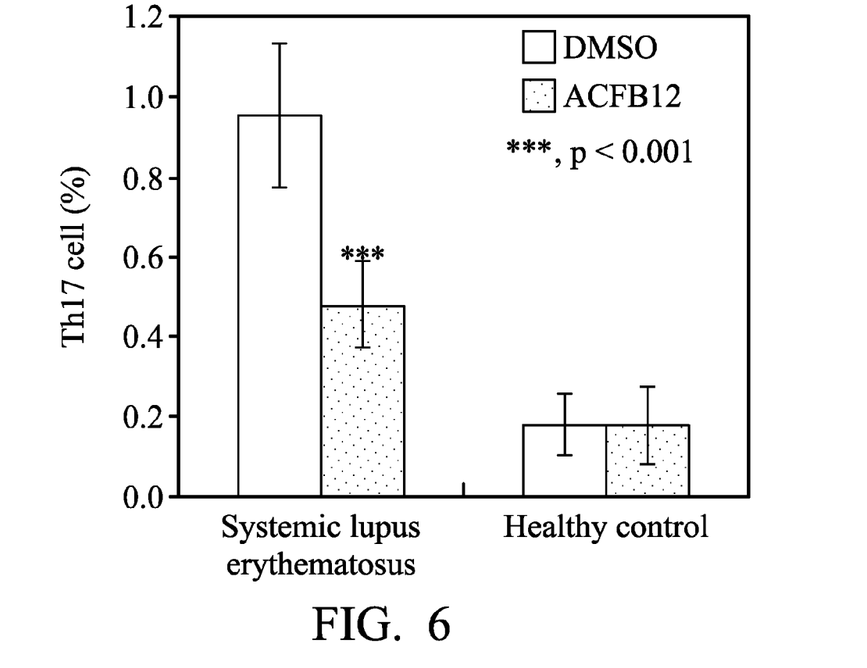
FIG. 6 shows the effect of *Antrodia cinnamomea* extract, ACFB12, on Th17 cells of systemic lupus erythematosus (SLE) patients according to one embodiment of the invention, ***: $p<0.001$.

The experimental results of FIG. 6 show that, at a concentration of 20 ng/ml, the fruiting body extract of *Antrodia cinnamomea*, ACFB12, is capable of reducing the Th17 cells in systemic lupus erythematosus patients, effectively (mean: 0.48% vs. 0.95%; p<0.001), while the fruiting body extract of *Antrodia cinnamomea*, ACFB12, has no effect on the Th17 cells in healthy controls.

Example 5

Effect of Fruiting Body Extract of *Antrodia cinnamomea*, ACFB12, on Th17 Cells of Graves' Disease Patient In this experiment, through peripheral blood mononuclear cells (PBMCs) of a Graves' Disease patient, the effect of the fruiting body extract of *Antrodia cinnamomea*, ACFB12, on Th17 cells of a Graves' Disease patient was evaluated. The procedure for the experiment is shown in the following:

Peripheral blood of 5 Graves' Disease patients and 3 healthy people was collected, and then the mononuclear cells therein were isolated. After that, the isolated mononuclear cells were treated with ACFB12 (20 μg/ml) (experimental group) or DMSO (control group) for 72 hours, and then intracellular staining was performed on the mononuclear cells with the IL-17 antibody. Finally the stained mononuclear cells were analyzed to determine the percentage of Th17 cells present therein. The experimental results are shown in FIG. 7.

Figure 7:
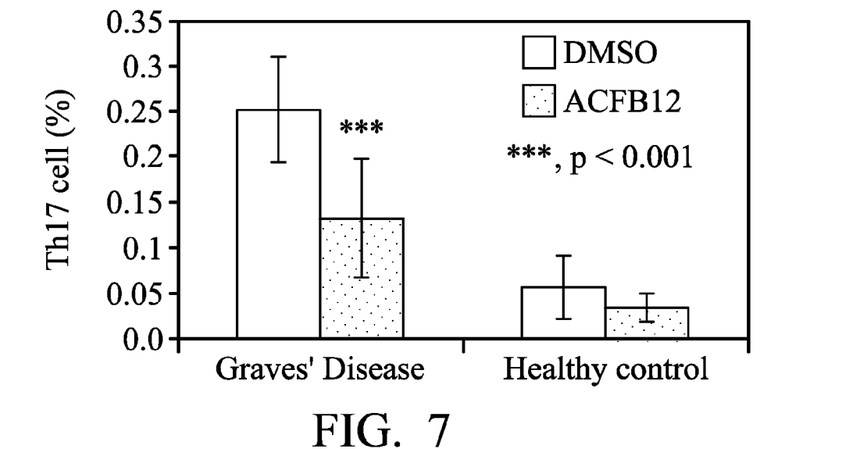
FIG. 7 shows the effect of *Antrodia cinnamomea* extract, ACFB12, on Th17 cells of Graves' Disease patients according to one embodiment of the invention, ***: $p<0.001$.

The experimental results of FIG. 7 show that at a concentration of 20 μg/ml, the fruiting body extract of *Antrodia cinnamomea*, ACFB12, is capable of reducing Th17 cells in Graves' Disease patients (mean: 0.13% vs. 0.25%; p<0.001), but has no significant effect on Th17 cells in healthy controls (mean: 0.04% vs. 0.06%; p=0.161).

Example 6

Effect of Fruiting Body Extract of *Antrodia cinnamomea*, ACFB12, on Th17 Cells in an Animal Model of Psoriasis Induced by Imiquimod In this experiment, through an animal model of psoriasis induced by imiquimod, the effect of the fruiting body extract of *Antrodia cinnamomea*, ACFB12, on Th17 cells was evaluated. The procedure for the experiment is shown in the following:

First, the hair on the back of Balb/c mice (6-8 weeks old) was shaved off, and then the mice were grouped into three groups which were the naïve group, control group and experimental group. For the naïve group, there was no treatment applied to the mice. For the control group, 62.5 mg imiquimod cream (Aldara; 3M Pharmaceuticals) was applied on the back of each mouse. Administration of imiquimod was performed once a day for 10 consecutive days, to induce psoriasis-like skin inflammation. For the experimental group, 62.5 mg imiquimod cream was applied on the back of each mouse, and then fruiting body extract of *Antrodia cinnamomea*, ACFB12 (10 mg/kg), was injected into each mouse, intraperitoneally. Administration of imiquimod and administration of *Antrodia cinnamomea*, ACFB12 (10 mg/kg), were performed once a day for 10 consecutive days. After that, the mice were sacrificed and then the spleens thereof were taken and passed through a 70 μm mesh to obtain a single-cell suspension. Red blood cells in the single-cell suspension were removed by a red blood cell lysis buffer, and then the single-cell suspension was washed twice with PBS buffer to obtain primary spleen lymphocytes. The spleen lymphocytes ($2 \times 10^6$) were implanted into a 24-well culture plate coated with anti-CD3 monoclonal antibody (1 μg/ml) (BD Pharmingen) to stimulate the lymphocytes for 24 hours. After that, the cells were collected and dissolved in 0.2% BSA/PBS buffer, and stained with anti-mouse CD4 PE antibody for 30 minutes. Then, the cells were washed 3 times with PBS buffer. The cells were further fixed and permeabilized with 2% paraformaldehyde and 0.5% saponin. After that, intracellular staining was performed to the cells with IL-17 FITC antibody. Finally the stained cells were analyzed to determine the percentage of $CD4^+/IL-17^+$ double positive cells present therein by a flow cytometer (FACSCalibur; BD Biosciences) and CellQuest software (BD Biosciences). The experimental results are shown in FIG. 8

Figure 8:
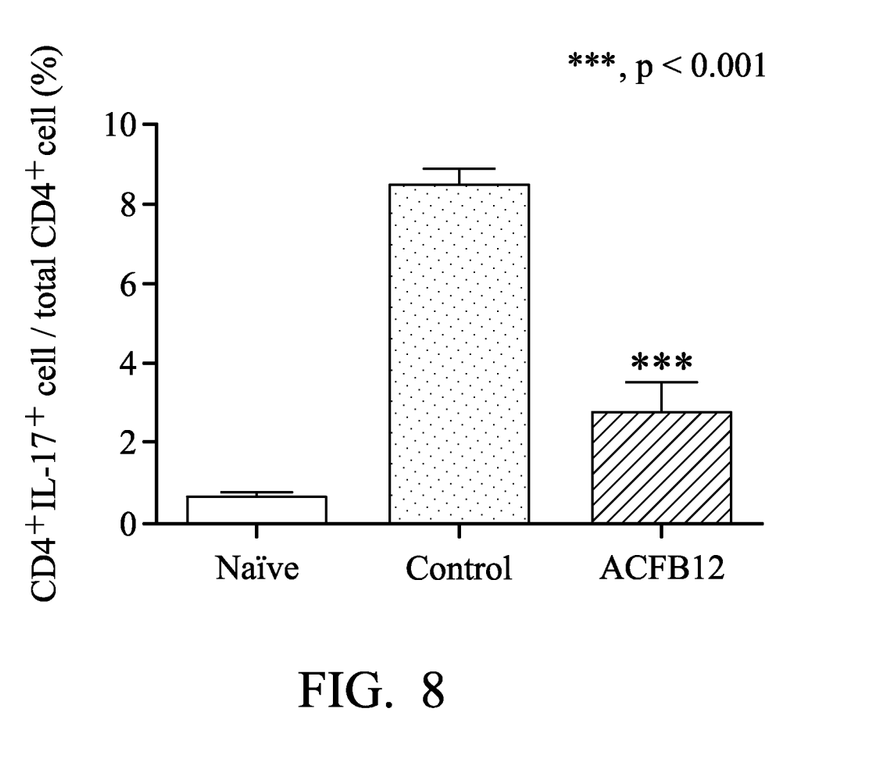
FIG. 8 shows the effect of *Antrodia cinnamomea* extract, ACFB12, on Th17 cells in animal models of psoriasis induced by imiquimod (IMQ) according to one embodiment of the invention, ***: $p<0.001$.

FIG. 8 shows that, as compared with the naïve group, for the control group, after administration of imiquimod, the $CD4^+/IL-17^+$ double positive cells therein can be increased. However, for the experimental group, after administration of imiquimod and administration of *Antrodia cinnamomea*, ACFB12, the $CD4^+/IL-17^+$ double positive cells therein can be reduced compared to the control group (mean: 3.6% vs. 9.3%; p<0.001).

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for inhibiting differentiation of CD4+ T cells to Th17 cells, comprising:
    administering an effective amount of a fruiting body extract of *Antrodia cinnamomea* to a subject in need thereof, wherein the fruiting body extract of *Antrodia cinnamomea* has an effect of inhibiting differentiation of CD4+ T cells to Th17 cells,
    wherein the fruiting body extract of *Antrodia cinnamomea* is obtained by performing an extraction process on a fruiting body of *Antrodia cinnamomea*, and wherein a 10-95% ethanol aqueous solution is used in the extraction process, wherein the extraction process comprises:

refluxing the fruiting body of *Antrodia cinnamomea* with the 10-95% ethanol aqueous solution to form a mixture; and filtering the mixture to obtain a filtrate, wherein the filtrate is the fruiting body extract of *Antrodia cinnamomea*.

2. The method for inhibiting differentiation of CD4+ T cells to Th17 cells, as claimed in claim 1, wherein the subject in need thereof is suffering from a disease selected from the group consisting of: systemic lupus erythematosus (SLE), Graves' Disease, rheumatoid arthritis (RA), psoriasis, type 1 diabetes (T1DM), Hashimoto's thyroiditis, multiple sclerosis (MS), inflammatory bowel disease, allergic diseases, and acquired immunodeficiency disease.

3. A method for treating systemic lupus erythematosus (SLE), comprising:

administering an effective amount of a fruiting body extract of *Antrodia cinnamomea* to a subject in need thereof, wherein the fruiting body extract of *Antrodia cinnamomea* has an effect of inhibiting differentiation of Th17 cells, wherein the fruiting body extract of *Antrodia cinnamomea* is obtained by performing an extraction process on a fruiting body of *Antrodia cinnamomea*, and wherein a 10-95% ethanol aqueous solution is used in the extraction process, wherein the extraction process comprises:

refluxing the fruiting body of *Antrodia cinnamomea* with the 10-95% ethanol aqueous solution to form a mixture; and filtering the mixture to obtain a filtrate, wherein the filtrate is the fruiting body extract of *Antrodia cinnamomea*.

4. The method for treating systemic lupus erythematosus (SLE), as claimed in claim 3, wherein the systemic lupus erythematosus comprises active systemic lupus erythematosus.

* * * * *